United States Patent
Mizuno (10) Patent No.: US 8,605,978 B2
(45) Date of Patent: Dec. 10, 2013

(54) MEDICAL IMAGE PROCESSING APPARATUS AND METHOD, AND COMPUTER READABLE RECORDING MEDIUM ON WHICH IS RECORDED PROGRAM FOR THE SAME

(75) Inventor: Osamu Mizuno, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 396 days.

(21) Appl. No.: 13/013,385

(22) Filed: Jan. 25, 2011

(65) Prior Publication Data

US 2011/0243403 A1 Oct. 6, 2011

(30) Foreign Application Priority Data

Mar. 31, 2010 (JP) ................................ 2010-084389

(51) Int. Cl.
*G06K 9/00* (2006.01)
*G06K 9/46* (2006.01)

(52) U.S. Cl.
USPC ........... 382/131; 382/128; 382/130; 382/132; 382/181; 382/190; 382/259

(58) Field of Classification Search
USPC .......... 382/131, 128, 130, 132, 181, 190, 259
See application file for complete search history.

(56) References Cited

U.S. PATENT DOCUMENTS

| | | | |
|---|---|---|---|
| 7,286,694 B2 | 10/2007 | Oosawa | |
| 7,372,983 B2 * | 5/2008 | Bruijns | 382/130 |
| 7,447,344 B2 * | 11/2008 | Pichon et al. | 382/130 |
| 7,583,829 B2 | 9/2009 | Kiraly et al. | |
| 7,715,608 B2 | 5/2010 | Vaz et al. | |
| 8,224,057 B2 * | 7/2012 | Hong et al. | 382/132 |
| 2003/0103665 A1 * | 6/2003 | Uppaluri et al. | 382/131 |
| 2006/0056685 A1 * | 3/2006 | Kiraly et al. | 382/165 |
| 2006/0229513 A1 * | 10/2006 | Wakai | 600/407 |
| 2009/0096787 A1 | 4/2009 | Masumoto et al. | |

FOREIGN PATENT DOCUMENTS

| | | |
|---|---|---|
| EP | 1988511 | 11/2008 |
| JP | 2005-028121 | 2/2005 |
| JP | 2008253293 | 10/2008 |

OTHER PUBLICATIONS

"Mishima et al., Complexity of Terminal Airspace Geometry Assessed by Ling Computed Tomography in Normal Subjects and Paitents With Chronic Obstructive Pulmonary Disease", Proc Natl., Acad. Sci USA,, vol. 96, pp. 8829-8834, 1999.
Nakamura et al., Automated Classification of Pulmonary Artery and Vein From Chest X-Ray CT Images by Tree Structures Analysis, Technical Report of IEICE, MI Japan Jan. 21, 2006, vol. 105, No. 580, pp. 105-108.

(Continued)

*Primary Examiner* — Michael A Newman
(74) *Attorney, Agent, or Firm* — Young & Thompson (57) ABSTRACT

Extracting a branch structure and a surrounding structure area in which a surrounding structure of the branch structure exists from a three-dimensional medical image, setting an attention branch structure in the branch structure, estimating an attention surrounding structure area functionally associated with the attention branch structure from the surrounding structure area based on the branch structure, obtaining an evaluation value in the attention surrounding structure area, and generating a mapped image which is an image generated by mapping the evaluation value in the attention surrounding structure area to a morphological image representing morphology of at least one of the attention branch structure and the attention surrounding structure area.

11 Claims, 7 Drawing Sheets

(56) References Cited

OTHER PUBLICATIONS

Hayashi et al., "Development of the Procedure for Automatic Extracting Interlobar Fissures and Its Performance Evaluation" Technical Report of IEICE, MI2003-53(Oct. 2003), Medical Image, Oct. 31, 2003, vol. 103, No. 409, pp. 39-44.

Masutani et al., "Computerized Detection of Pulmonary Embolism in Spiral CT Angiography Based O Volumetric Image Analysis", IEEE Transaction on Medial Imaging, vol. 21, No. 12, pp. 1517-1523, 2002.

Kobayashi et al., Trial of Branch Base Tree Structure Model Construction for Blood Vessel Geometric Representation. Mar. 9, 2005, Riken Japan Riken Symposium, Digitization and Database Construction Research of Organism Shape Information, pp. 84-92.

Hirano et al., Qualification of Shrinkage of Lung Lobes in Chest CT Images Using the 3D Voronoi Division and Application to Tumor Discrimination, Jul. 2001, JMIT 20th annual meeting proceedings, pp. 315-316.

Kinsella et al., "Quantitation of Emphysema by Computed Tomography Using a "Density Mask" Program and Correlation With Pulmonary Function Tests", test 97, pp. 315-321, 1990.

Rueckert et al., "Nonrigid Registration Using Free-Form Deformations: Appplication to Breast MR Images", IEEE Transactions on Medical Imaging, vol. 18, No. 8, pp. 712-721, 1999.

Extended European Search Report dated Jan. 18, 2013 in corresponding European Patent Application No. 11152585.3.

* cited by examiner

MEDICAL IMAGE PROCESSING APPARATUS AND METHOD, AND COMPUTER READABLE RECORDING MEDIUM ON WHICH IS RECORDED PROGRAM FOR THE SAME

BACKGROUND OF THE INVENTION

1. Field of the Invention

The present invention relates to an apparatus and method for performing image processing on a three-dimensional medical image representing a subject's internal structure having a branch structure and a surrounding structure, such as a lung. The invention also relates to a computer readable recording medium on which is recorded a program for the same.

2. Description of the Related Art

An image processing method for diagnosing embolization of a pulmonary blood vessel based on a three-dimensional medical image representing a chest region is known.

For example, U.S. Pat. No. 7,583,829 proposes a method in which a pulmonary blood vessel system is divided into segments, then an embolization area in the pulmonary blood vessel system after the segmentation is identified manually or automatically, a blood vessel sub-tree affected by the identified embolization is analyzed to identify a lung area affected by the embolization, and the lung area is visually displayed.

Further, U.S. Pat. No. 7,715,608 proposes a method in which segmentation of pulmonary parechymal tissue is performed on a CT image representing both lungs, then a perfusion map of the segmented image is generated, and an abnormally underperfused area is rendered and displayed comparatively opaque.

The method described in U.S. Pat. No. 7,583,829, however, only visualizes a lung area affected by embolization of a pulmonary blood vessel and does not indicate how the pulmonary function has been changed in the area.

In the mean time, it is difficult to locally evaluate pulmonary function, like a lung area affected by the embolization of a pulmonary blood vessel, by the method described in U.S. Pat. No. 7,715,608 since the method visualizes a perfusion map of the entire lungs.

The present invention has been developed in view of the circumstances described above and it is an object of the present invention to provide a medical image processing apparatus and method that allows, based on a three-dimensional medical image representing a subject's internal structure having a branch structure and a surround structure, easy observation or evaluation for functional and/or morphological characteristics of an area of the surrounding structure functionally associated with an attention portion of the branch structure. It is a further object of the present invention to provide a computer readable recording medium on which is recorded a medical image processing program of the present invention.

SUMMARY OF THE INVENTION

A medical image processing apparatus of the present invention is an apparatus, including:

a branch structure extraction means for extracting a branch structure from a three-dimensional medical image representing a subject's internal structure having the branch structure and a surrounding structure which is a structure located around and functionally associated with the branch structure;

a surrounding structure area extraction means for extracting a surrounding structure area which includes the surrounding structure from the three-dimensional medical image;

an attention branch structure setting means for setting an attention branch structure which is an attention portion of the branch structure;

an attention surrounding structure area estimation means for estimating an attention surrounding structure area functionally associated with the attention branch structure from the surrounding structure area based on the branch structure;

an evaluation value obtaining means for obtaining an evaluation value of function and/or morphology of the subject's internal structure in the estimated attention surrounding structure area; and a mapped image generation means for generating a mapped image which is an image generated by mapping the evaluation value in the attention surrounding structure area to a morphological image generated from the three-dimensional medical image and representing morphology of at least one of the attention branch structure and the attention surrounding structure area.

A medical image processing method of the present invention is a method, including the steps of:

extracting a branch structure from a three-dimensional medical image representing a subject's internal structure having the branch structure and a surrounding structure which is a structure located around and functionally associated with the branch structure;

extracting a surrounding structure area which includes the surrounding structure from the three-dimensional medical image;

setting an attention branch structure which is an attention portion of the branch structure;

estimating an attention surrounding structure area functionally associated with the attention branch structure from the surrounding structure area based on the branch structure;

obtaining an evaluation value of function and/or morphology of the subject's internal structure in the estimated attention surrounding structure area; and generating a mapped image which is an image generated by mapping the evaluation value in the attention surrounding structure area to a morphological image generated from the three-dimensional medical image and representing morphology of at least one of the attention branch structure and the attention surrounding structure area.

A computer readable recording medium on which is recorded a medical image processing program of the present invention is a medium having a program recorded thereon for causing a computer to perform the method described above.

The term "branch structure" as used herein refers to a subject's internal structure having a branching structure. A specific example may be a blood vessel.

The term "surrounding structure" as used herein refers to a structure that performs a certain function of the subject's internal structure with the branch structure. A specific example of the "certain function" is an exchange of a predetermined substance carried by a fluid flowing through the branch structure between the surrounding structure and the branch structure.

A specific example of the "subject's internal structure" is a lung. In this case, the branch structure can be a blood vessel or a bronchus, the surrounding structure can be lung parenchyma, and the surrounding structure area can be a lung field area. Further, the pulmonary blood vessel can be either a pulmonary artery or a pulmonary vein.

A specific example of the "attention branch structure" is a portion of the branch structure from an embolization site to the periphery.

The "attention branch structure" may be set based on a user manual specifying operation in an image generated from the three-dimensional medical image, by automatically using an image analysis/recognition method, or by a combination thereof. Specific examples of the combined method may include a method in which a reference point (e.g., embolization site) of an attention branch structure is specified by a user manual operation and a predetermined image analysis/recognition process is performed based on the reference point, thereby automatically extracting the attention branch structure, and a method in which an attention branch structure is selected by a user manual operation from attention branch structure candidates automatically extracted by a predetermined image analysis/recognition process or an attention branch structure is corrected by a user manual operation.

It is conceivable that the "attention surrounding structure area" is estimated based on morphological characteristics of the branch structure, such as the positional relationship between the attention branch structure and non-attention branch structure in the branch structure, tube diameter of the branch structure, and the like. Further, where the subject's internal structure is a lung, the lung represented by the three-dimensional medical image may be divided into a plurality of predetermined lung sections and the attention surrounding structure area may be estimated so as to belong within one of the divided lung sections.

With regard to the "evaluation value", the entirety of the attention surrounding structure area may have one evaluation value or each of a plurality of sub-areas constituting the attention surrounding structure area may have one evaluation value. The sub-area may be an area of a plurality of pixels or an area of one pixel.

Further, the "evaluation value" may be calculated based the three-dimensional medical image, the processing target image of the present invention, or an evaluation value calculated based on another medical image representing the same subject's internal structure may be obtained as the evaluation value. Here, the "another medical image" may be an image captured by the same modality as that of the three-dimensional medical image, the processing target image of the present invention, at a different time or an image captured by a different modality. Further, an evaluation value calculated based on certain measurement data with respect to the same subject's internal structure may be obtained as the evaluation value. When an evaluation value based on another medical image or measurement data are used, in particular, it is preferable that position alignment is performed so that the position of the subject's internal structure represented by the evaluation value matches with the corresponding position in the mapping destination morphological image.

The "mapped image" may be a broad mapped image generated by mapping the evaluation value in the attention surrounding structure area to a broad morphological image representing morphology of an area of the subject's internal structure which includes, as a part, the attention branch structure and the attention surrounding structure area. Further, an arrangement may be adopted in which an evaluation value is obtained for each sub-area constituting an area of the subject's internal structure which includes, as a part, the attention surrounding structure area, and a broad mapped image is generated by mapping each evaluation value to an area of the broad morphological image corresponding to the area where each evaluation value is obtained, in which a boundary between the attention surrounding structure area and a surrounding structure area other than the attention surrounding structure area is made distinguishable.

A specific example of the method of mapping the evaluation may be a method in which an evaluation value is obtained for each of a plurality of sub-areas constituting the attention surrounding structure area and each evaluation value in the attention surrounding structure area is projected onto each surface pixel of the attention surrounding structure area. In this case, with respect to each of a plurality of straight lines connecting at least a portion of the attention branch structure and each surface pixel of the attention surrounding structure area, a pixel value to be mapped to each surface pixel on each straight line may be determined based on the evaluation value of the sub-area on each straight line.

According to the present invention, a branch structure and a surrounding structure are extracted from a three-dimensional medical image representing a subject's internal structure, an attention branch structure is set in the branch structure, then an attention surrounding structure area functionally associated with the attention branch structure is estimated from the surrounding structure area, an evaluation value in the attention surrounding structure area is obtained, and a mapped image, which is an image generated by mapping the evaluation value in the attention surrounding structure area to a morphological image representing morphology of at least one of the attention branch structure and the attention surrounding structure area, is generated. This allows functional and/or morphological characteristics of the surrounding structure area functionally associated with the attention branch structure to be observed or evaluated easily, thereby contributing to the improvement of diagnostic accuracy and efficiency.

For example, when a portion of a branch structure from an embolization site to the periphery is set as the attention branch structure, mapping of the evaluation to the surrounding structure area functionally associated with the attention branch structure in the morphological image allows a local influence of the embolization of the branch structure on the surrounding structure to be observed or evaluated easily.

Where a broad morphological image representing morphology of an area of the subject's internal structure which includes, as a part, the attention branch structure and the attention surrounding structure area is generated, functional and/or morphological characteristics may be observed or evaluated while understanding the positional relationship between the attention branch structure or attention surrounding structure and an adjacent structure.

Further, when an evaluation value is obtained for each sub-area constituting an area of the subject's internal structure which includes, as a part, the attention surrounding structure area and a broad mapped image is generated by mapping each evaluation value to an area of the broad morphological image corresponding to the area where each evaluation value is obtained, in which a boundary between the attention surrounding structure area and a surrounding structure area other than the attention surrounding structure area is made distinguishable, comparison in functional and/or morphological characteristics between the attention branch structure or attention surrounding structure and an adjacent structure may be made easily, whereby functional and/or morphological characteristics of the attention surrounding structure may be observed or evaluated more easily.

Still further, if a mapped image is generated by projecting evaluation values of a plurality of sub-areas constituting an attention surrounding structure area onto surface pixels of the attention surrounding structure area, functional and/or morphological characteristics of the attention surrounding structure area may be understood three-dimensionally.

DESCRIPTION OF THE PREFERRED EMBODIMENTS

Hereinafter, a medical image diagnosis system that employs a medical image processing apparatus according to an embodiment of the present invention will be described by taking, as example, the case in which influence of embolization of a pulmonary blood vessel on a surrounding lung parenchymal area is observed or evaluated based on a CT image of a human chest.

Figure 1:
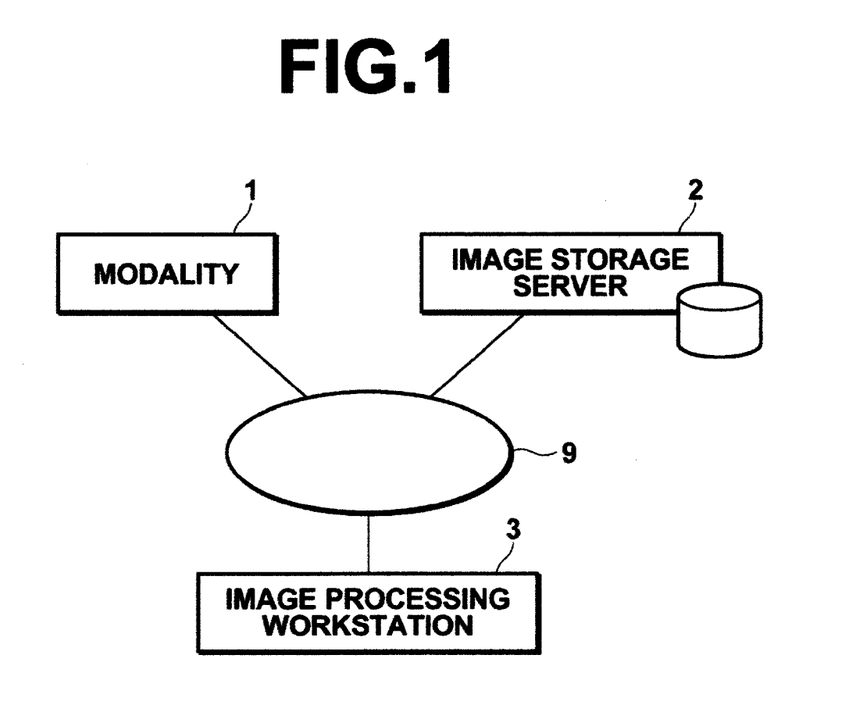
FIG. 1 is a schematic configuration diagram of a medical image diagnosis system in which a medical image processing apparatus according to an embodiment of the present invention is implemented.

FIG. 1 is a hardware configuration diagram of the medical image diagnosis system, illustrating an overview thereof. As shown in FIG. 1, the system includes modality 1, image storage server 2, and image processing workstation 3 which are communicatably connected to each other via network 9.

Modality 1 includes an apparatus for imaging an inspection target region of a subject to generate image data representing a three-dimensional medical image of the region and outputting the image data by attaching auxiliary information defined in DICOM (Digital Imaging and Communication in Medicine) standard as image information. Specific examples of the apparatus include, for example, CT, MRI, and the like. In the present embodiment, a description will be made of a case in which three-dimensional image data representing a chest region of a human body to be examined are generated by scanning the human body with CT in a body axis direction.

Image storage server 2 is a computer for storing medical image data, in a database, obtained by modality 1 and image data of a medical image generated by image processing in image processing workstation 3 and managing them, and includes a large capacity external memory unit and database management software (e.g., Object Relational Database (ORDB)).

Image processing workstation 3 is a computer that performs, in response to a request from a radiology reader, image processing (including image analysis) on medical image data obtained from modality 1 or image storage server 2 and displays a generated image. It is provided with known hardware devices, such as a CPU, a main storage unit, an auxiliary storage unit, an input/output interface, a communication interface, input devices (mouse, keyboard, and the like), a display device (display monitor), a data bus, and the like, and has a known operating system installed thereon. The medical image process is implemented in the image processing workstation 3 and the process is realized by executing a program installed from a recording medium, such as a CD-RCM or the like. Alternatively, the program may be a program installed after being downloaded from a storage unit of a server connected via a network, such as Internet or the like.

The storage format of image data and communication between each component of the system are based on the DICOM protocol or the like.

Figure 2:
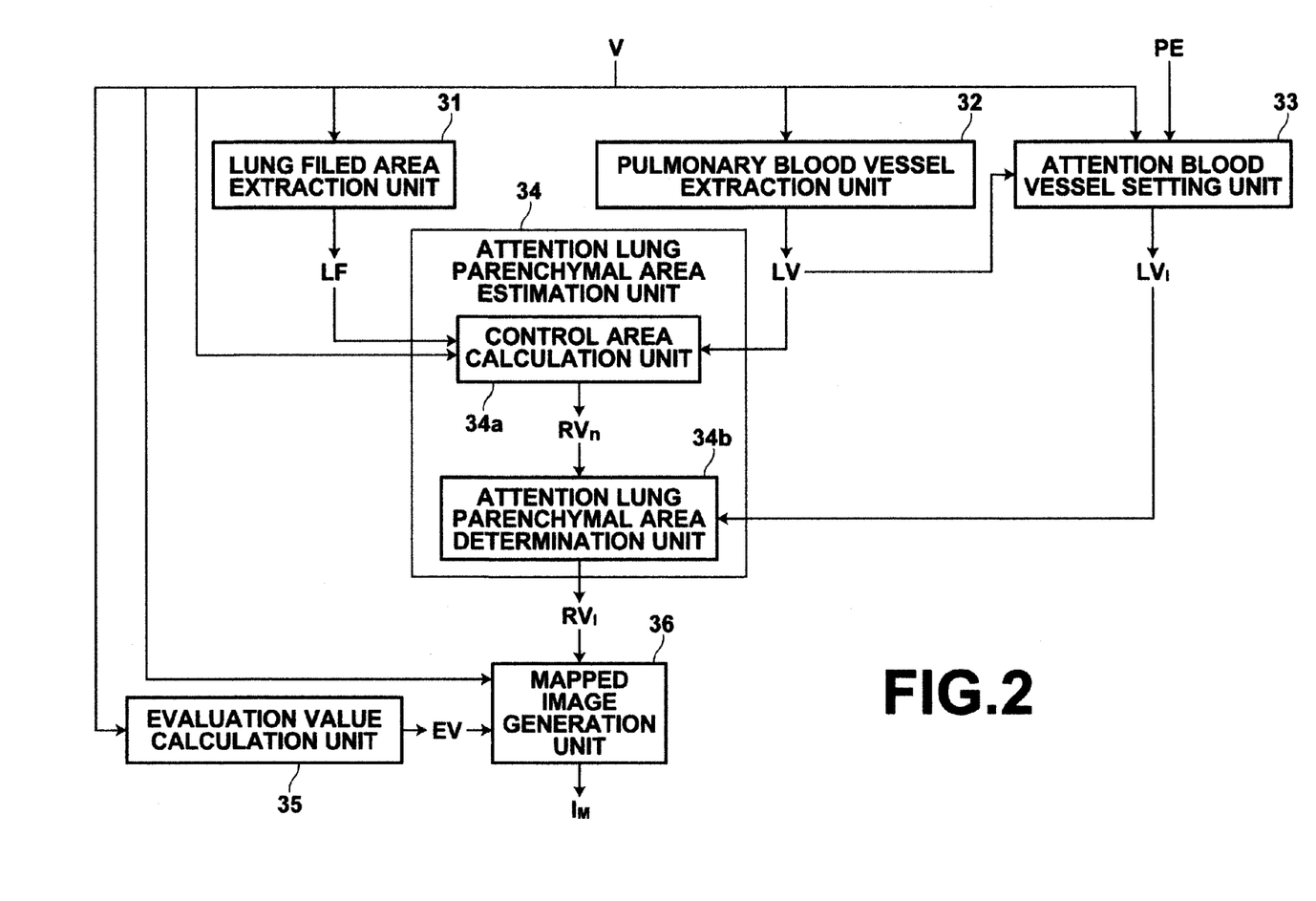
FIG. 2 is a block diagram schematically illustrating a configuration and a process flow for realizing a medical image processing function according to an embodiment of the present invention.

FIG. 2 is a block diagram illustrating a portion of the function of image processing workstation 3 relevant to the medical image processing according to the first embodiment of the present invention. As shown in FIG. 2, the medical image processing according to an embodiment of the present invention is realized by lung field area extraction unit 31, pulmonary blood vessel extraction unit 32, attention blood vessel setting unit 33, attention lung parenchymal area estimation unit 34, evaluation value calculation unit 35, and mapped image generation unit 36. In FIG. 2, the three-dimensional medical image V, attention site (embolization site) PE, lung field area LF, pulmonary blood vessel structure LV, attention blood vessel structure $LV_I$, control area $RV_n$ with respect to each blood vessel, attention lung parenchymal area $RV_I$, evaluation value EV, mapped image $I_M$ are data written into and read out from a predetermined memory area of image processing workstation 3 by each of the processing units described above.

Lung field area extraction unit 31 extracts a lung field area LF of a subject using each of a plurality of axial cross-sectional images constituting a three-dimensional medical image V as input. For example, as the lung field area LF is an area having a pixel value corresponding to the CT value of air, an air area in the subject may be extracted as the lung field area after discriminating between the air area around the subject and the subject area by performing threshold processing on each axial cross-sectional image.

Pulmonary blood vessel extraction unit 32 extracts a pulmonary blood vessel structure LV using the three-dimensional medical image V as input. More specifically, region growing is performed to extract a mass of pixels within a pulmonary blood vessel area, then a thinning process is performed on the extracted pulmonary blood vessel area, and based on the obtained thin line representing a pulmonary blood vessel, each pixel on the thin line is classified into an end point, an edge (side), or a branch point, whereby tree-structure data representing the pulmonary blood vessel can be obtained. Further, characteristic amounts, such as blood vessel diameter at each pixel on the thin line, length of each edge (blood vessel branch), and the like, may also be stored as the tree-structure data, as required (for details, refer to a literature "Trial of branch base tree structure model construction for blood vessel geometric representation" by D. Kobayashi et al., [Online], Mar. 9, 2005, RIKEN, Japan, RIKEN symposium, Digitization and database construction research of organism shape information, pp. 84-92, [Date of Retrieval: Jan. 6, 2010], Internet <URL: http://www.comp-bio.riken.jp/keijyo/products/2005_1_files/kobayashi_print.pdf>, and a literature "Automated Classification of Pulmonary Artery and Vein from Chest X-ray CT Images by Tree Structure Analysis" by S. Nakamura et al., Technical Report of IEICE, MI, Japan, Jan. 21, 2006, Vol. 105, No. 580, pp. 105-108, [Date of Retrieval: Nov. 20, 2009], Internet <URL: http://www.murase.nuie.nagoya-u.ac.jp/~ide/res/paper/J05-kenkyukai-snake-1.pdf> (Reference Document 1)).

Attention blood vessel setting unit 33 sets an attention blood vessel structure $LV_I$ in the pulmonary blood vessel structure LV. The attention blood vessel structure $LV_I$ represents a blood vessel structure from an embolization site to the periphery. More specifically, attention blood vessel setting unit 33 causes a two-dimensional image generated from the three-dimensional medical image V to be displayed on the display device of image processing workstation 3, and receives a user operation specifying an attention site (embolization site) PE in the pulmonary blood vessel structure LV. Then, attention blood vessel setting unit 33 sets a blood vessel structure from the specified attention site PE to the periphery as the attention blood vessel structure $LV_I$ based on the tree-structure of the blood vessel structure LV (for details, refer to Reference Document 1).

Attention lung parenchymal area estimation unit 34 includes control area calculation unit 34a and attention lung parenchymal area determination unit 34b, and estimates an attention lung parenchymal area $RV_I$ in a lung parenchymal area around the pulmonary blood vessel functionally associated with the attention blood vessel structure $LV_I$ based on the pulmonary blood vessel structure LV.

Figure 3:
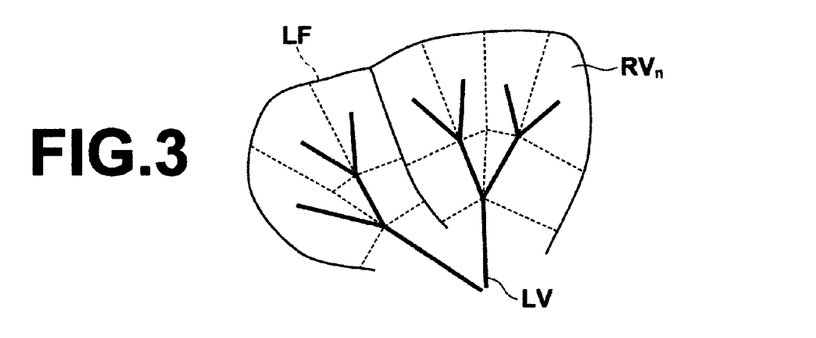
FIG. 3 illustrates a control area with respect to each pulmonary blood vessel branch.

Control area calculation unit 34a performs three-dimensional Voronoi division using a blood vessel structure as the kernel point mass to obtain a control area $RV_n$ of each blood vessel branch constituting the pulmonary blood vessel structure LV. More specifically, as schematically illustrated in FIG. 3, control area calculation unit 34a identifies one of the blood vessel branchs constituting the pulmonary blood vessel structure LV located closest to each pixel in the lung field area LF, that is, identifies by which of the blood vessel branches each pixel in the lung field area LF is controlled. As a result, an area controlled by the same blood vessel branch is determined to be the control area of the blood vessel branch. This yields a control area $RV_n$ with respect to each blood vessel branch (for details, refer to "Quantification of shrinkage of lung lobes in chest CT images using the 3D Voronoi division and application to tumor discrimination" by Y. Hirano et al., [Online], July 2001, JMIT $20^{th}$ annual meeting proceedings, pp. 315-316, [Date of Retrieval: Nov. 20, 2009], Internet <URL: http://mase.itc.nagoya-u.ac.jp/~hirano/Papers/JAMIT2001.pdf>).

In the mean time, attention lung parenchymal area determination unit 34b determines an area of the control areas $RV_n$ controlled by the attention blood vessel structure $LV_I$ to be the attention lung parenchymal area $RV_I$.

Evaluation value calculation unit 35 calculates an evaluation value EV for pulmonary function and morphology based on the three-dimensional medical image V. Here, evaluation value calculation unit 35 performs a known perfusion analysis using the three-dimensional medical image V as input and calculates a local peripheral average density for each pixel in the lung parenchymal area. More specifically, evaluation value calculation unit 35 extracts a lung parenchymal area by removing a bronchus and the pulmonary blood vessel structure LV and performing local averaging using a three-dimensional Gaussian kernel as the smoothing operator (for details, refer to U.S. Pat. No. 7,715,608).

Figure 4A:
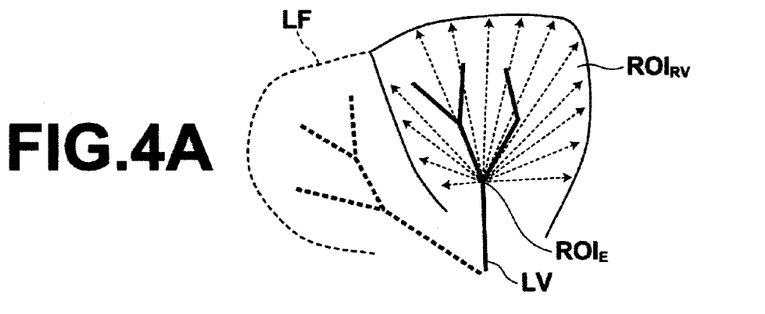
FIG. 4A schematically illustrates a first method of mapping an evaluation value at each point in an attention pulmonary parenchymal area to each point on the surface of the attention lung parenchymal area.
Figure 5A:
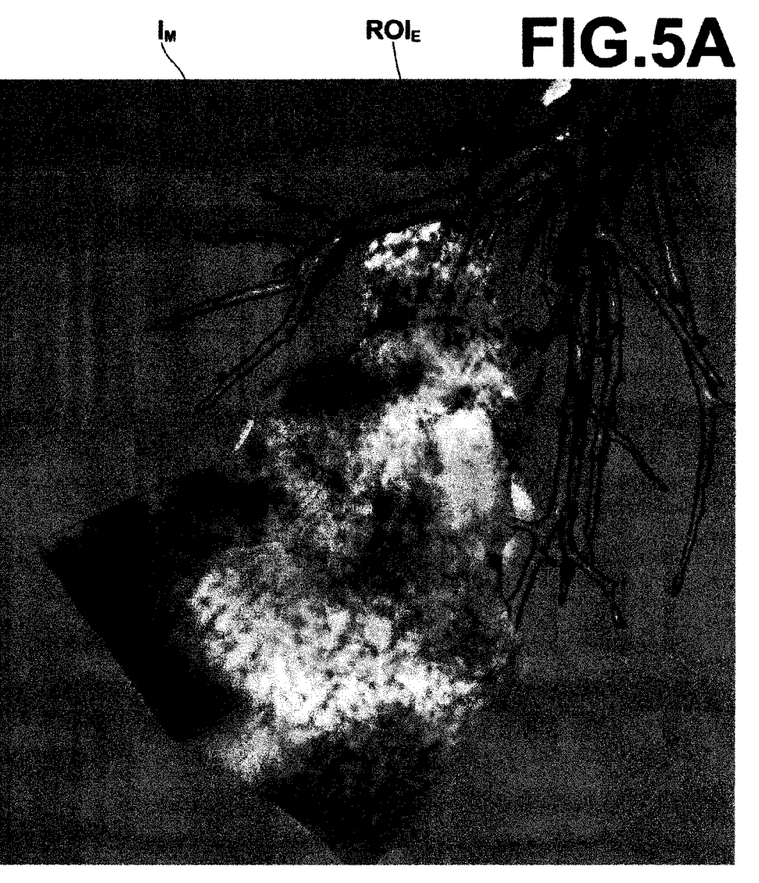
FIG. 5A illustrates a first example of a mapped image generated in an embodiment of the present invention.

Mapped image generation unit 36 generates a mapped image $I_M$ which is an image generated by mapping an evaluation value EV of the attention lung parenchymal area $RV_I$ to a morphological image representing the attention blood vessel structure $LV_I$ and an adjacent portion of the blood vessel structure LV based on the three-dimensional medical image V. FIG. 5A shows an example of mapped image $I_M$, which is an image generated by superimposing a evaluation image obtained by projecting an evaluation value of the attention lung parenchymal area $RV_I$ controlled by the attention blood vessel structure $LV_I$ (from the attention site PE to the periphery) onto the surface of the attention lung parenchymal area $RV_I$ and made semitransparent, on a volume rendering image representing the attention blood vessel structure $LV_I$ and an adjacent portion of the pulmonary blood vessel structure LV. Here, as schematically illustrated in FIG. 4A, the luminance value projected onto the surface of the attention lung parenchymal area $RV_I$ can be obtained by radially sampling evaluation values EV from the attention site PE to each point on the surface of the attention lung parenchymal area $RV_I$. That is, a representative value (e.g., average value) of evaluation values EV of respective points on each of a plurality of straight lines connecting the attention site PE and each point on the surface of the attention lung parenchymal area $RV_I$ is obtained, and a luminance value representing a color or a density according to the representative value is allocated to each point on the surface of the attention lung parenchymal area $RV_I$. The image in which the volume rendering image and evaluation value image are superimposed on top of each other may be obtained in the following manner. That is, allocating a predetermined luminance value to each pixel representing the attention blood vessel structure $LV_I$ in the three-dimensional medical image V and an adjacent portion of the pulmonary blood vessel structure LV and opacity to each pixel of the evaluation value image, then setting an alpha value to each corresponding position between the three-dimensional medical image V and evaluation value image based on the opacity allocated to the evaluation value image, and performing volume rendering using alpha blending with respect to each position for the luminance value allocated to the three-dimensional medical image V and a luminance value of the evaluation value image (for details, U.S. Patent Application Publication No. 20090096787 proposed by the present applicant and the like).

Figure 6:
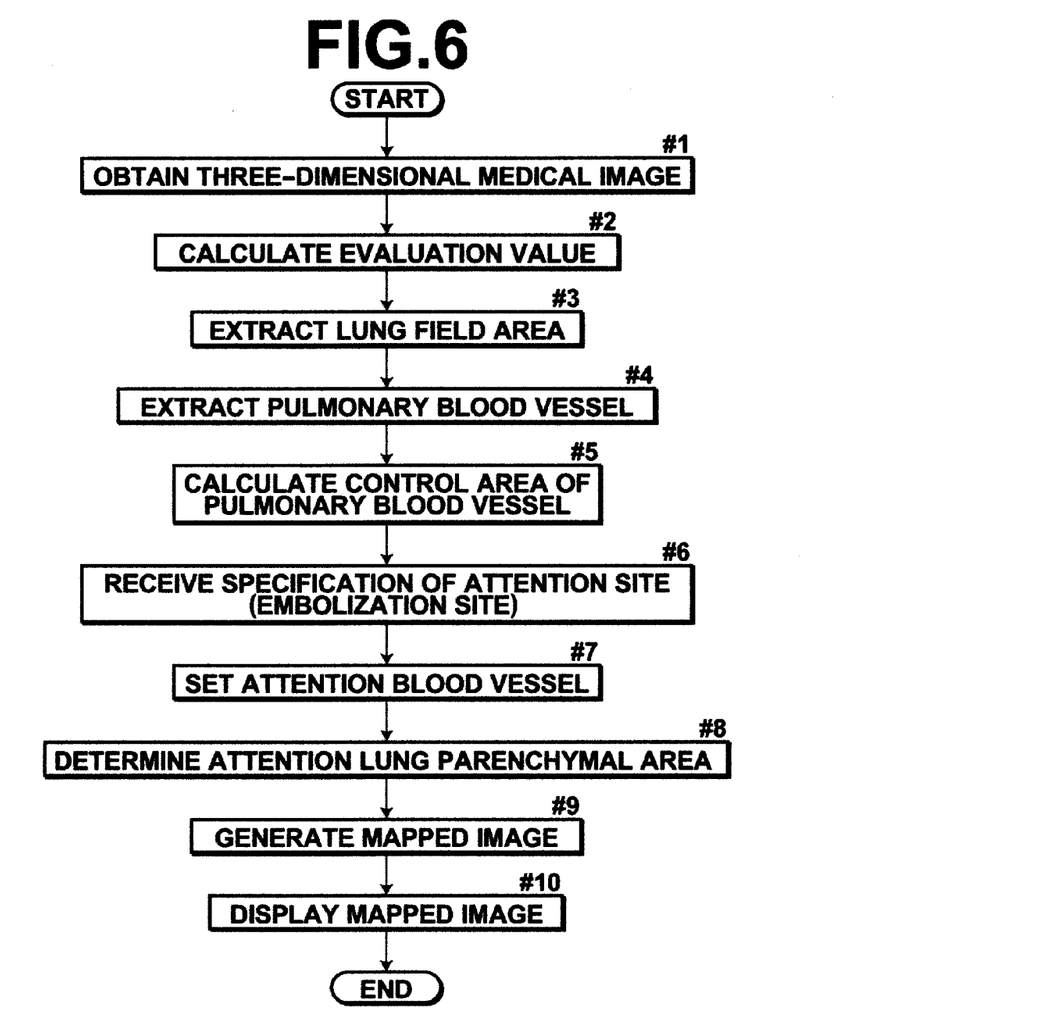
FIG. 6 is a flowchart illustrating a flow of image processing using the medical image diagnosis system according to an embodiment of the present invention.

A flow of image diagnosis using the medical image processing according to the embodiment of the present invention will now be described. FIG. 6 is a flowchart illustrating a flow of user operation, calculation processing, display processing, and the like performed under the execution of medical image processing software according to the embodiment of the present invention.

First, image data of a three-dimensional medical image V is obtained (#1). The three-dimensional medical image V is an image captured by modality 1 and stored in image storage server 2 based on an examination order from a doctor of a requesting department. The user makes a request for obtaining a processing target three-dimensional medical image data V by operating a terminal operation interface of a known ordering system implemented in image processing workstation 3. In response to the operation, image processing workstation 3 sends a request for retrieval of the three-dimensional medical image data V to image storage server 2. Then, image storage server 2 obtains the processing target three-dimensional medical image data V by performing database searching and sends the data to image processing workstation 3.

Image processing workstation 3 obtains the three-dimensional medical image data V sent from image storage server 2.

In image processing workstation 3, evaluation value calculation unit 35 calculates a local peripheral average density (evaluation value EV) of each pixel in a lung parenchymal area (#2), lung field area extraction unit 31 extracts a lung field area LF of the subject using each of a plurality of axial cross-sectional images constituting the three-dimensional medical image V as input (#3), and pulmonary blood vessel extraction unit 32 extracts a pulmonary blood vessel structure LV using the three-dimensional medical image V as input (#4). Then, based on the lung field area LF extracted by lung field area extraction unit 31 and the pulmonary blood vessel structure LV extracted by pulmonary blood vessel extraction unit 32, control area calculation unit 34a of attention lung parenchymal area estimation unit 34 obtains a control area $RV_n$ with respect to each blood vessel branch constituting the pulmonary blood vessel structure LV using the three-dimensional medical image V as input (#5).

Next, attention blood vessel setting unit 33 receives a user operation specifying an attention site (embolization site) PE in the pulmonary blood vessel structure LV (#6) and, based on the tree-structure of the pulmonary blood vessel structure LV, sets a portion of the blood vessel structure LV from the specified attention site PE to the periphery as an attention blood vessel structure $LV_I$ (#7).

Attention lung parenchymal area determination unit 34b of attention lung parenchymal area estimation unit 34 determines an area of the control areas $RV_n$ calculated by control area calculation unit 34a controlled by the attention blood vessel structure $LV_I$ set by attention blood vessel setting unit 33 to be an attention lung parenchymal area $RV_I$ (#8).

Then, mapped image generation unit 36 generates a mapped image $I_M$ which is an image generated by mapping an evaluation value EV of the attention lung parenchymal area $RV_I$ to a morphological image representing the attention blood vessel structure $LV_I$ and an adjacent portion of the blood vessel structure LV based on the three-dimensional medical image V (#9), and the generated mapped image $I_M$ is displayed on the display device of image processing workstation 3 (#10).

In the embodiment of the present invention, a mapped image $I_M$ which is a morphological image representing an attention blood vessel structure $LV_I$ and an adjacent portion of the blood vessel structure LV with an evaluation value EV of the attention lung parenchymal area $RV_I$ being mapped is generated by the series of processing described above. This allows a local influence of embolization of the blood vessel structure LV on a lung parenchymal area around thereof to be observed or evaluated easily, thereby contributing to the improvement of diagnostic accuracy and efficiency.

Further, the morphological image represents not only the attention blood vessel structure $LV_I$ but also an adjacent portion of the pulmonary blood vessel structure LV, so that a local influence of embolization may be observed or evaluated while understanding the positional relationship between the attention blood vessel structure $LV_I$ or attention lung parenchymal area $RV_I$ and an adjacent portion of the pulmonary blood vessel structure LV.

Further, mapped image generation unit 36 generates a mapped image $I_M$ by projecting an evaluation value of each pixel in the attention lung parenchymal area $RV_I$ onto each surface pixel of the attention parenchymal area $RV_I$, so that functional and/or morphological characteristics of the attention parenchymal area $RV_I$ may be understood three-dimensionally.

In projecting evaluation values EV, luminance values of surface pixels are determined through radial sampling from the attention site PE, as illustrated in FIG. 4A. This results in that the evaluation value EV is projected onto each point on the surface of the attention lung parenchymal area $RV_I$ in a direction different from the visual line of the mapped image $I_M$, so that the generated mapped image $I_M$ is appropriate for observing the distribution of evaluation values EV adjacent to the attention blood vessel LV $_I$.

The embodiment described above is illustration purposes only and should not be construed as limiting the scope of the technical scope of the present invention.

It should be appreciated that various modifications and changes made to the system configuration, processing flow, module structure, specific processing contents, and the like in the embodiment described above without departing from the spirit of the present invention are included in the scope of the present invention.

For example, with respect to the system configuration, a description has been made of a case in which various types of processing in FIG. 2 is performed by a single image processing workstation 3, but the system may be configured such that the various types of processing is distributed to a plurality of workstations and performed in cooperation with each other.

With respect to the processing flow, step #2 in the flowchart of FIG. 6 may be performed at any timing after step #1 and before step #9 or in parallel with steps #3 to #8.

With respect to specific processing content, lung field extraction unit 31 may extract a lung field area LF by other known extraction methods, such as the method proposed by the present applicant in Japanese Unexamined Patent Publication No. 2008-253293.

Likewise, pulmonary blood vessel extraction unit 32 may employ various types of known blood vessel extraction methods other than that described above. In that case, if a tree-structure is obtained simultaneously with the extraction, the obtained tree-structure may be used directly in the subsequent processing without performing a thinning process. Further, as for a preferable modification of pulmonary blood vessel extraction, pulmonary blood vessel extraction unit 32 is configured to extract only either one of the pulmonary artery or pulmonary vein. More specifically, only either one of the pulmonary artery or pulmonary vein may be extracted in the following manner by focusing attention on the fact that the pulmonary artery and bronchus run in parallel near the center of each section of a lung while the pulmonary vein runs near the boundary of each section of the lung, that is, between the bronchi. That is, an extracted blood vessel structure is broken down into a plurality of blood vessel branch groups based on the contact relationship between blood vessels and a bronchus is also extracted using a known method by the pulmonary blood vessel extraction unit 32. Then, using the extracted bronchus as a kernel point mass, three-dimensional Voronoi division is performed to estimate a boundary plane of lung segments, then an average distance from the bronchus and an average distance from the boundary plane are calculated for each blood vessel branch group, and a blood vessel branch group located close to the bronchus and away from the boundary plane of lung sections is classified into the pulmonary artery, while a blood vessel branch group located away from the bronchus and close to the boundary plane of lung sections is classified into the pulmonary vein (for details, refer to Reference Document 1 described above). In the lung parenchyma, gas exchange in the blood occurs with both the pulmonary artery and pulmonary vein. Therefore, if both the pulmonary artery and pulmonary vein are extracted by pulmonary blood vessel extraction unit 32 without distinction between them and a control area is calculated by control area calculation unit 34a using both the pulmonary artery and pulmonary vein, as in the embodiment described above, the lung parenchymal area is divided into a control area controlled by the pulmonary artery and a control area controlled by the pulmonary vein, resulting in a division improper to the lung parenchyma function. Consequently, when only either one of the pulmonary artery and the pulmonary vein is extracted by pulmonary blood vessel extraction unit 32, as in the modification, a division of the lung parenchymal area which is highly consistent with the lung parenchyma function may be achieved, although it may be necessary to separately perform the observation or evaluation of attention lung parenchymal area for each of the pulmonary artery and pulmonary vein.

Attention blood vessel setting unit 33 may be configured to automatically recognize an embolization site in the pulmonary blood vessel structure LV using a known method. For example, a method for extracting an embolization site by analyzing, in a pulmonary blood vessel structure LV extracted by pulmonary blood vessel extraction unit 32, three-dimensional characteristic amounts, such as the blood vessel size, local contrast using a morphological filter, geometrical characteristics, such as the curvature using quadratic differential, volume, length, and the like is known (for details, a literature "Computerized Detection of Pulmonary Embolism in Spiral CT Angiography Based on Volumetric Image analysis" by Y. Masutani et al., IEEE Transactions on Medical Imaging, Vol. 21, No. 12, pp. 1517-1522, 2002).

In the embodiment described above, control area calculation unit 34a of attention lung parenchymal area estimation unit 34 may be configured to obtain one control area $RV_n$ for a group of a plurality of blood vessel branches or to further break down one blood vessel branch into portions and obtain a control area $RV_n$ with respect to each portion of the broken down blood vessel branch, instead of obtaining an control area $RV_n$ with respect to each blood vessel branch. Further, the control area $RV_n$ may be obtained based on characteristic amounts, such as the diameter of the blood vessel and the like, and pixel values stored in the tree structure data of the pulmonary blood vessel structure LV, as well as the distance between a pixel in the lung field area LF and the blood vessel branch.

When control area $RV_n$ is obtained by performing Voronoi division on the entire lung field area LF, the control area $RV_n$ may sometimes cross over a boundary of lung lobes, so that control area calculation unit 34a may be configured to separate the lung field area LF into lung lobes (five lobes of right upper lobe, right middle lobe, right lower lobe, left upper lobe, left middle lobe, and left lower lobe) in advance and to calculate the control area $RV_n$ within each lung lobe. Here, the separation method of lung lobes may be automatic or manual. As for the automatic separation method, any known method may be used, such as a method in which locations of interlobar fissures are roughly identified using structural information of trachea, bronchus, pulmonary blood vessel, then the interlobar fissures are extracted using density information, and lung lobes are separated based on the extracted interlobar fissures. (For details, refer to a literature "Development of the Procedure for Automatic Extracting Interlobar Fissures and its Performance Evaluation" by T. Hayashi et al., Technical Report of IEICE, MI2003-53 (2003-10), Medical Image, Oct. 31, 2003, Vol. 103, No. 409, pp. 39-44, [Date of Retrieval: Jan. 1, 2010], Internet, <URL: http://www.fjt.info.gifu-u.ac.jp/publication/328.pdf>.) A pulmonary blood vessel never interacts with the lung parenchyma in two or more lung lobes, so that limitation of the extent of control area $RV_n$ within each lung lobe in the manner as described above allows a mapped image which is consistent with the anatomical structure of a lung and is more appropriate for diagnosis to be obtained. As the pulmonary artery is located away from the boundary of each section, if attention lung parenchymal area $RV_I$ is estimated based on a control area $RV_n$ determined based only on blood vessel information, the estimation accuracy may be degraded in comparison with the case in which the pulmonary vein is used. Estimation of the attention lung parenchymal area $RV_I$ using also each of the sections described above allows the estimation accuracy to be improved.

As for the evaluation value calculated by evaluation value calculation unit 35, the following known items may be cited and used as appropriate according to diagnostic purposes or the like other than the local peripheral average density used in the embodiment described above.

(a) Perfusion parameters obtainable from time density curves obtained in a plurality of regions of interest in a CT perfusion analysis, such as pulmonary blood flow, pulmonary blood volume, mean transit time, and the like.

(b) Pixel values of a plurality of radiation images, obtained by one type of apparatus, such as a CT or the like, representing transmission/attenuation degrees of a plurality of radiation patterns having different energy distributions in a subject respectively. Alternatively, a difference in pixel value between a plurality of images (captured by emitting different energies from a plurality of radiation sources, captured by emitting radiation from one radiation source by changing the energy, captured by exposing, once, a plurality of radiation detectors stacked on top of each other via an additional filter, such as an energy separation filter to change the energy distribution of radiation transmitted through the subject by one exposure and detecting radiation of different energy distributions by the plurality of radiation detectors).

(c) Pixel values of pulmonary functional images obtained by CT and other modalities, such as PET, MRI, lung perfusion scintigraphy, lung ventilation scintigraphy, and the like.

(d) A difference in pixel value between a plurality of images before and after the administration of a contrast agent or a plurality of images captured at different times after the administration of a contrast agent.

(e) A local ventilation volume, such as a difference in pixel value between a plurality of ventilation images obtained between inhalation and exhalation or before and after inhalation of a predetermined gas (for details, refer to Japanese Unexamined Patent Publication No. 2005-028121).

(f) A displacement amount at each position in a lung field between inhalation and exhalation (refer to U.S. Pat. No. 7,286,694 filed by the present applicant). A displacement amount may be obtained for each pixel in a bronchus or a control area and an average value or a maximum value may be used as the evaluation value.

(g) A volume ratio of emphysema to lung parenchymal area in a control area. For example, an area of a lung field where pixel values are less than a predetermined threshold value (threshold value of −960 HU for a non-contrast enhanced CT image) is determined to be emphysema (for details, refer to a literature "Quantitation of emphysema by computed tomography using a "density mask" program and correlation with pulmonary function tests" by M. Kinsella et al., Chest, 97, pp. 315-321, 1990), and based on the volume of the determined emphysema area, an emphysema ratio is obtained as an evaluation value by Emphysema Ratio=Volume of Emphysema Area in Control Area/Volume of Control Area.

(h) An emphysema cluster size in a control area

As in (g) above, an emphysema area is determined by threshold processing and a volume of each connected component (cluster) in the emphysema area is obtained. Further, a fractal dimension D is calculated for each connected component (for details, refer to a literature "Complexity of terminal airspace geometry assessed by lung computed tomography in normal subjects and patients with chronic obstructive pulmonary disease" by M. Mishima et al., Proc. Natl. Acad. Sci. USA, Vol. 96, pp. 8829-8834, 1999).

(i) An amount of temporal variation of evaluation value obtained in each item above.

A difference in evaluation value of each item described above obtained from a plurality of images/measurement values captured/measured at different times is used as the evaluation value.

(j) A ratio of an evaluation value obtained in each item above to an average value of evaluation values of each item in the entire non-embolized area.

Note that for those involving calculation between a plurality of images captured at different times, such as between inhalation and exhalation or captured by different modalities, the position of a subject or a structure is different between the images due to misalignment of the bodily position of the subject or cardiac/pulmonary contractions at the times of imaging. Therefore, it is necessary to perform position alignment processing in order to align the positional relationship. As for the position alignment processing, any known rigid or non-rigid registration method may be used. The non-rigid registration includes, for example, a method in which two corresponding points are specified by the user, a method that performs the alignment based on the image contrast without using a landmark, or the like (for details, refer to Japanese Unexamined Patent Publication No. 2005-028121 and a literature "Nonrigid Registration Using Free-Form Deformations: Application to Breast MR Images" by D. Rueckert et al., IEEE Transactions on Medical Imaging, Vol. 18, No. 8, pp. 712-721, 1999, and the like). Further, a bronchus may be extracted and the extracted bronchus may be used as the land mark when non-rigid registration is performed.

In the embodiment described above, mapped image generation unit 36 obtains each pixel value projected onto the surface of the attention lung parenchymal area $RV_I$ by radially sampling evaluation values from the attention site PE to each point on the surface of the attention lung parenchymal area $RV_I$, as schematically illustrated in FIG. 4A. But the sampling may be performed from the center of gravity of the attention lung parenchymal area $RV_I$ or the like to each point on the surface of the attention lung parenchymal area $RV_I$.

Figure 4B:
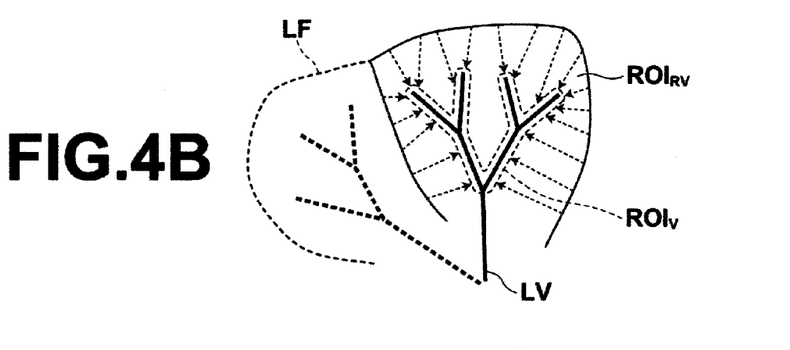
FIG. 4B schematically illustrates a second method of mapping an evaluation value at each point in an attention pulmonary parenchymal area to each point on the surface of the attention lung parenchymal area.
Figure 4C:
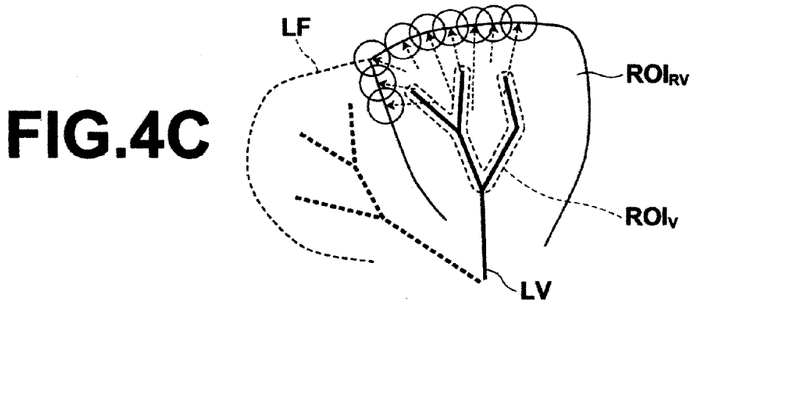
FIG. 4C schematically illustrates a third method of mapping an evaluation value at each point in an attention pulmonary parenchymal area to each point on the surface of the attention lung parenchymal area.

Further, as for the sampling method, a method that identifies a point on the attention blood vessel structure $LV_I$ nearest each point on the surface of the attention lung parenchymal area $RV_I$ and samples the evaluation value of each point between the two points, as schematically illustrated in FIG. 4B, may be used. Still further, as schematically illustrated in FIG. 4C, a point on the surface of the attention lung parenchymal area $RV_I$ nearest each of the pixels in the attention lung parenchymal area $RV_I$ is identified and the evaluation value EV of each of the pixels is mapped to points on the surface within a predetermined radius centered on the identified point.

In the embodiment described above, when determining, from each sampled point, a luminance value of the corresponding point on the surface of the attention lung parenchymal area $RV_I$, an average value of the evaluation value EV of each sampled point is calculated, but various representative values, such as a maximum value, a minimum value, a median value, a weighted sum, and the like, may be used.

Further, if the evaluation value EV is a value obtained under a different positional relationship between coordinate axes and the subject, mapped image generation unit 36 may obtain the positional correspondence relationship between the three-dimensional medical image V and evaluation value image by performing the rigid or non-rigid registration process described above.

Still further, a morphological image generated from the three-dimensional medical image V may be an image other than the volume rendering image, such as a MIP image, a MPR image, or the like.

When a morphological image generated from the three-dimensional medical image V and an evaluation value image are superimposed on top of each other, if the opacity allocated to each pixel of the evaluation value image is made changeable by a user operation, it is possible to make the surface of the attention lung parenchymal area $RV_I$ semi-transparent to observe the attention blood vessel structure $LV_I$ in the attention lung parenchymal area $RV_I$ or otherwise to make the surface opaque not to observe the attention blood vessel structure $LV_I$ in the attention lung parenchymal area $RV_I$.

Further, as for the method of superimposing the morphological image and evaluation value image, a method in which the luminance value of each position of the mapped image may be calculated through simple addition, subtraction, or multiplication of luminance values of each corresponding position between the morphological image and evaluation value image, instead of the alpha blending process of the two images as in the embodiment described above. Alternatively, a luminance value of each position of the morphological image and evaluation value image is alternately allocated to each corresponding pixel of the mapped image to combine the two images in a checkered pattern. Further, the two images may be combined by alternately allocating luminance values of each line of the morphological image and evaluation value image to each corresponding line of the mapped image.

Figure 5B:
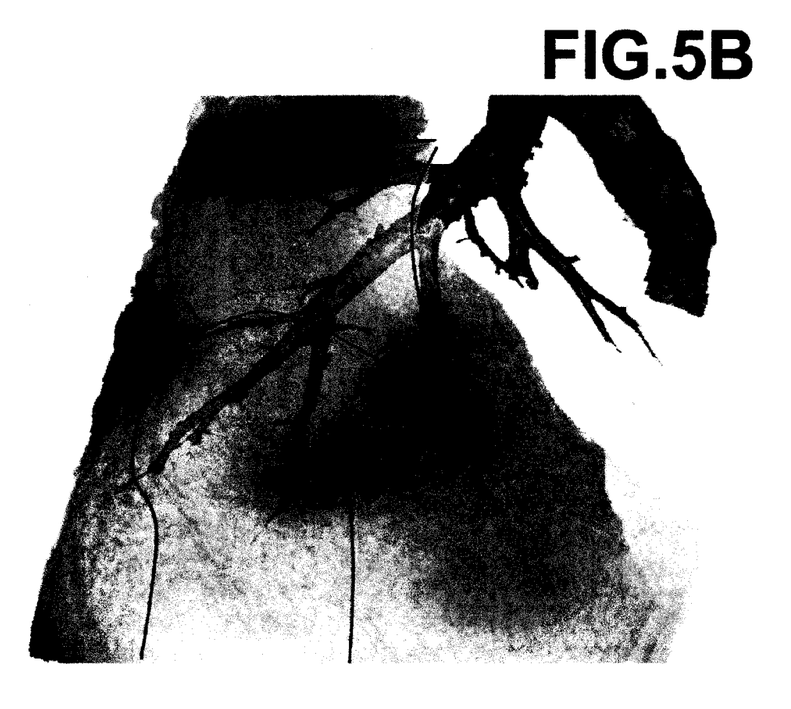
FIG. 5B illustrates a second example of a mapped image generated in an embodiment of the present invention.

Still further, as shown by way of example in FIG. 5B, mapped image generation unit 36 may be configured to generate an evaluation value image for a broader area than that of the attention lung parenchymal area $RV_I$ and attention blood vessel structure $LV_I$, and when the morphological image based on the three-dimensional medical image V and evaluation value image are superimposed on top of each other, a boundary line or the like may be added to a boundary between the attention lung parenchymal area $RV_I$ and an area in the lung field area LF other than the attention lung parenchymal area $RV_I$.

Figure 5C:
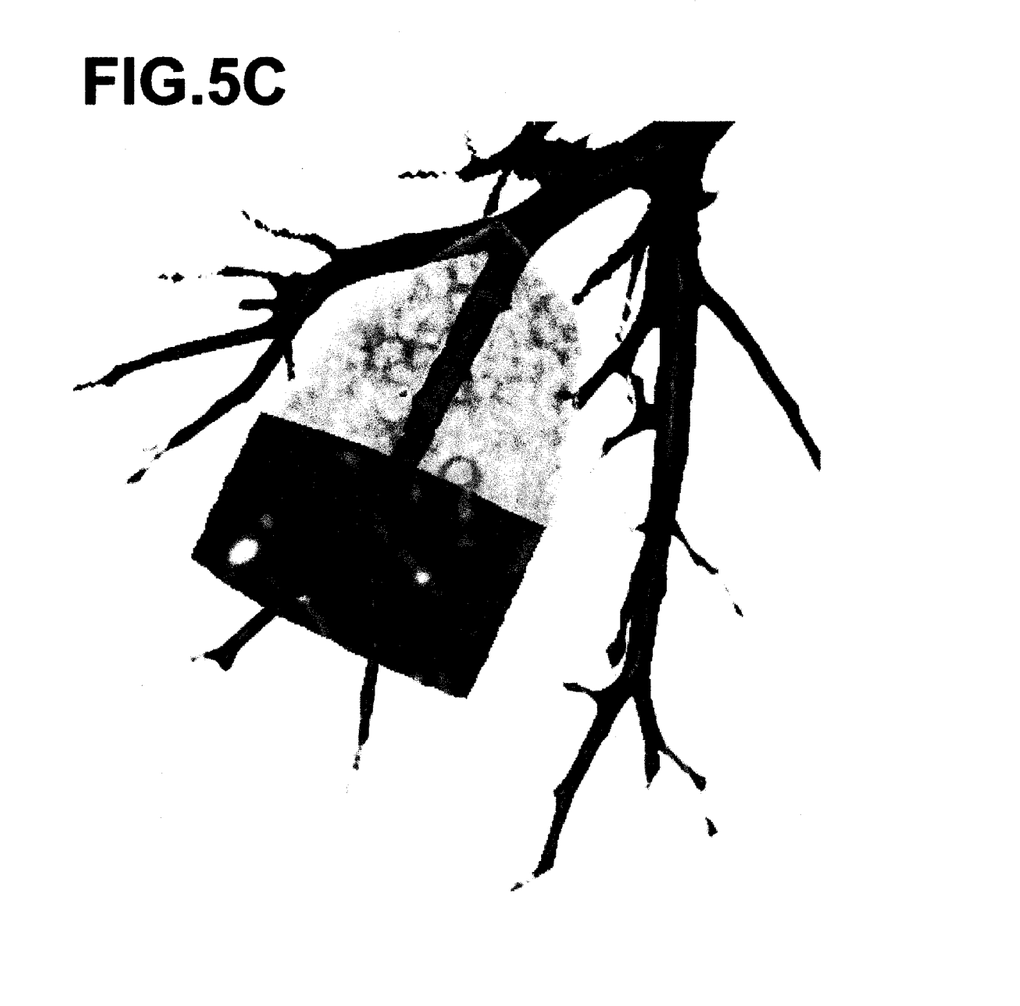
FIG. 5C illustrates a third example of a mapped image generated in an embodiment of the present invention.

Further, as shown by way of example in FIG. 5C, mapped image generation unit 36 may be configured to three-dimensionally clip a portion of the attention lung parenchymal area $RV_I$ and to paste an image (monochrome display of the original image, another image after non-rigid registration) or an evaluation value on the clipped boundary surface.

Still further, in the embodiment described above, the description has been made of a case in which a human lung is used as the observation or evaluation target, but an arrangement may be adopted in which another structure having a branch structure and a surrounding structure is observed or evaluated.

What is claimed is:

1. A medical image processing apparatus, comprising:
a branch structure extraction means for extracting a branch structure from a three-dimensional medical image representing a subject's internal structure having the branch structure and a surrounding structure which is a structure located around and functionally associated with the branch structure;
a surrounding structure area extraction means for extracting a surrounding structure area which includes the surrounding structure from the three-dimensional medical image;
an attention branch structure setting means for setting an attention branch structure which is an attention portion of the branch structure;
an attention surrounding structure area estimation means for estimating an attention surrounding structure area functionally associated with the attention branch structure from the surrounding structure area based on the branch structure;
an evaluation value obtaining means for obtaining an evaluation value of function and/or morphology of the subject's internal structure in the estimated attention surrounding structure area; and
a mapped image generation means for generating a mapped image which is an image generated by mapping the evaluation value in the attention surrounding structure area to a morphological image generated from the three-dimensional medical image and representing morphology of at least one of the attention branch structure and the attention surrounding structure area,
wherein the mapped image is an image generated by mapping the evaluation value in the attention surrounding structure area to a broad morphological image representing morphology of an area of the subject's internal structure which includes, as a part, the attention branch structure and the attention surrounding structure area, the image being generated by mapping each evaluation value to an area of the broad morphological image corresponding to the area where each evaluation value is obtained by the evaluation value obtaining means, in which a boundary between the attention surrounding structure area and a surrounding structure area other than the attention surrounding structure area is distinguishable, and
the evaluation value obtaining means is a means that obtains an evaluation value for each sub-area constituting an area of the subject's internal structure which includes, as a part, the attention surrounding structure area.

2. A medical image processing apparatus, comprising:
a branch structure extraction means for extracting a branch structure from a three-dimensional medical image representing a subject's internal structure having the branch structure and a surrounding structure which is a structure located around and functionally associated with the branch structure;
a surrounding structure area extraction means for extracting a surrounding structure area which includes the surrounding structure from the three-dimensional medical image;
an attention branch structure setting means for setting an attention branch structure which is an attention portion of the branch structure;
an attention surrounding structure area estimation means for estimating an attention surrounding structure area functionally associated with the attention branch structure from the surrounding structure area based on the branch structure;
an evaluation value obtaining means for obtaining an evaluation value of function and/or morphology of the subject's internal structure in the estimated attention surrounding structure area; and
a mapped image generation means for generating a mapped image which is an image generated by mapping the evaluation value in the attention surrounding structure area to a morphological image generated from the three-dimensional medical image and representing morphology of at least one of the attention branch structure and the attention surrounding structure area, wherein:
the evaluation value obtaining means is a means that obtains an evaluation value for each of a plurality of sub-areas constituting the attention surrounding structure area; and
the mapped image generation means is a means that performs the mapping by projecting each evaluation value in the attention surrounding structure area onto each surface pixel of the attention surrounding structure area.

3. The medical image processing apparatus of claim 2, wherein the mapped image generation means is a means that determines, with respect to each of a plurality of straight lines connecting at least a portion of the attention branch structure and each surface pixel of the attention surrounding structure area, a pixel value to be mapped to each surface pixel on each straight line based on the evaluation value of the sub-area on each straight line.

4. The medical image processing apparatus of claim 1, wherein the subject's internal structure is a lung.

5. The medical image processing apparatus of claim 4, wherein the surrounding structure is lung parenchyma.

6. The medical image processing apparatus of claim 5, wherein the surrounding structure area is a lung filled area.

7. The medical image processing apparatus of claim 1, wherein the branch structure is a blood vessel.

8. The medical image processing apparatus of claim 7, wherein the branch structure is either a pulmonary artery or a pulmonary vein.

9. A medical image processing apparatus, comprising:
a branch structure extraction means for extracting a branch structure from a three-dimensional medical image representing a subject's internal structure having the branch structure and a surrounding structure which is a structure located around and functionally associated with the branch structure;
a surrounding structure area extraction means for extracting a surrounding structure area which includes the surrounding structure from the three-dimensional medical image;
an attention branch structure setting means for setting an attention branch structure which is an attention portion of the branch structure;
an attention surrounding structure area estimation means for estimating an attention surrounding structure area functionally associated with the attention branch structure from the surrounding structure area based on the branch structure;
an evaluation value obtaining means for obtaining an evaluation value of function and/or morphology of the subject's internal structure in the estimated attention surrounding structure area; and
a mapped image generation means for generating a mapped image which is an image generated by mapping the evaluation value in the attention surrounding structure area to a morphological image generated from the three-dimensional medical image and representing morphology of at least one of the attention branch structure and the attention surrounding structure area, wherein the subject's internal structure is a lung, and the attention surrounding structure area estimation means is a means that divides the subject's internal structure represented in the three-dimensional medical image into a plurality of predetermined lung sections and estimates the attention surrounding structure area so as to belong within one of the divided lung sections.

10. A medical image processing method, comprising:

extracting a branch structure from a three-dimensional medical image representing a subject's internal structure having the branch structure and a surrounding structure which is a structure located around and functionally associated with the branch structure;

extracting a surrounding structure area which includes the surrounding structure from the three-dimensional medical image;

setting an attention branch structure which is an attention portion of the branch structure;

estimating an attention surrounding structure area functionally associated with the attention branch structure from the surrounding structure area based on the branch structure;

obtaining an evaluation value of function and/or morphology of the subject's internal structure in the estimated attention surrounding structure area; and generating a mapped image which is an image generated by mapping the evaluation value in the attention surrounding structure area to a morphological image generated from the three-dimensional medical image and representing morphology of at least one of the attention branch structure and the attention surrounding structure area, wherein the mapped image is an image generated by mapping the evaluation value in the attention surrounding structure area to a broad morphological image representing morphology of an area of the subject's internal structure which includes, as a part, the attention branch structure and the attention surrounding structure area, the image being generated by mapping each evaluation value to an area of the broad morphological image corresponding to the area where each evaluation value is obtained by the evaluation value obtaining means, in which a boundary between the attention surrounding structure area and a surrounding structure area other than the attention surrounding structure area is made distinguishable, and the evaluation value obtaining means is a means that obtains an evaluation value for each sub-area constituting an area of the subject's internal structure which includes, as a part, the attention surrounding structure area.

11. A non-transitory computer readable medium on which is recorded a medical image processing program for causing a computer to perform the method, comprising:

extracting a branch structure from a three-dimensional medical image representing a subject's internal structure having the branch structure and a surrounding structure which is a structure located around and functionally associated with the branch structure;

extracting a surrounding structure area which includes the surrounding structure from the three-dimensional medical image;

setting an attention branch structure which is an attention portion of the branch structure;

estimating an attention surrounding structure area functionally associated with the attention branch structure from the surrounding structure area based on the branch structure;

obtaining an evaluation value of function and/or morphology of the subject's internal structure in the estimated attention surrounding structure area; and generating a mapped image which is an image generated by mapping the evaluation value in the attention surrounding structure area to a morphological image generated from the three-dimensional medical image and representing morphology of at least one of the attention branch structure and the attention surrounding structure area, wherein the mapped image is an image generated by mapping the evaluation value in the attention surrounding structure area to a broad morphological image representing morphology of an area of the subject's internal structure which includes, as a part, the attention branch structure and the attention surrounding structure area, the image being generated by mapping each evaluation value to an area of the broad morphological image corresponding to the area where each evaluation value is obtained by the evaluation value obtaining means, in which a boundary between the attention surrounding structure area and a surrounding structure area other than the attention surrounding structure area is made distinguishable, and the evaluation value obtaining means is a means that obtains an evaluation value for each sub-area constituting an area of the subject's internal structure which includes, as a part, the attention surrounding structure area.

* * * * *